(12) United States Patent
King et al.

(10) Patent No.: US 6,268,727 B1
(45) Date of Patent: Jul. 31, 2001

(54) MEASUREMENT OF FLOW FRACTIONS FLOW VELOCITIES AND FLOW RATES OF A MULTIPHASE FLUID USING ESR SENSING

(75) Inventors: J. Derwin King; Qingwen Ni; Armando De Los Santos, all of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/103,064

(22) Filed: Jun. 23, 1998

Related U.S. Application Data
(60) Provisional application No. 60/050,637, filed on Jun. 24, 1997.

(51) Int. Cl.$^7$ ..................................................... G01V 3/00
(52) U.S. Cl. ........................... 324/306; 324/303; 324/300
(58) Field of Search .................................. 324/306, 303, 324/300, 307, 309, 318

(56) References Cited

U.S. PATENT DOCUMENTS

| | | | |
|---|---|---|---|
| 4,110,680 | 8/1978 | Bergmann et al. | 324/0.5 |
| 4,415,671 | 11/1983 | Nicksic | 436/29 |
| 4,531,093 | * 7/1985 | Rollwitz et al. | 324/300 |
| 4,536,711 | * 8/1985 | King et al. | 324/306 |
| 4,598,960 | 7/1986 | DiSanto et al. | 339/17 |
| 4,629,987 | 12/1986 | King et al. | 324/306 |
| 4,638,251 | 1/1987 | King | 324/306 |
| 4,782,295 | 11/1988 | Lew | 324/306 |
| 4,785,245 | 11/1988 | Lew et al. | 324/308 |
| 4,866,385 | 9/1989 | Reichwein | 324/300 |
| 4,889,540 | 12/1989 | Segerstrom et al. | 48/77 |
| 4,901,018 | 2/1990 | Lew | 324/306 |
| 5,122,746 | 6/1992 | King et al. | 324/307 |
| 5,216,366 | 6/1993 | Young | 324/307 |
| 5,539,309 | 7/1996 | Van Wyk et al. | 324/307 |
| 5,684,399 | * 11/1997 | Bayer | 324/306 |

FOREIGN PATENT DOCUMENTS

| | | | |
|---|---|---|---|
| AU-B-35308/84 | 11/1988 | (AU) | G01V/3/14 |
| DE 41 19 711 A | 12/1992 | (DE) . | |
| EP0 691 526 A1 | 10/1996 | (EP) | G01F/1/74 |
| GB 2 307 300 A | 5/1997 | (GB) | G01F/1/74 |

OTHER PUBLICATIONS

Coulthard, J., et al., Non–restrictive measurement of solids mass flowrate in pneumatic conveying systems, Measurement + Control, vol. 24, 113–119, May 1991.
PCT International Search Report.

\* cited by examiner

*Primary Examiner*—Christine Oda
*Assistant Examiner*—Brij B. Shrivastav
(74) *Attorney, Agent, or Firm*—Baker Botts L.L.P.

(57) ABSTRACT

Various flowmeters (10, 70, 110, 120) each have an ESR sensor (13, 73, 112, 121) for measuring the crude oil fraction and/or velocity of a fluid containing crude oil. In combination with an NMR sensor or other sensors, a complete set of flow fraction, flow velocity, and flow rate measurements can be obtained for multiphase fluids containing gas, oil, water or any combination thereof.

32 Claims, 6 Drawing Sheets

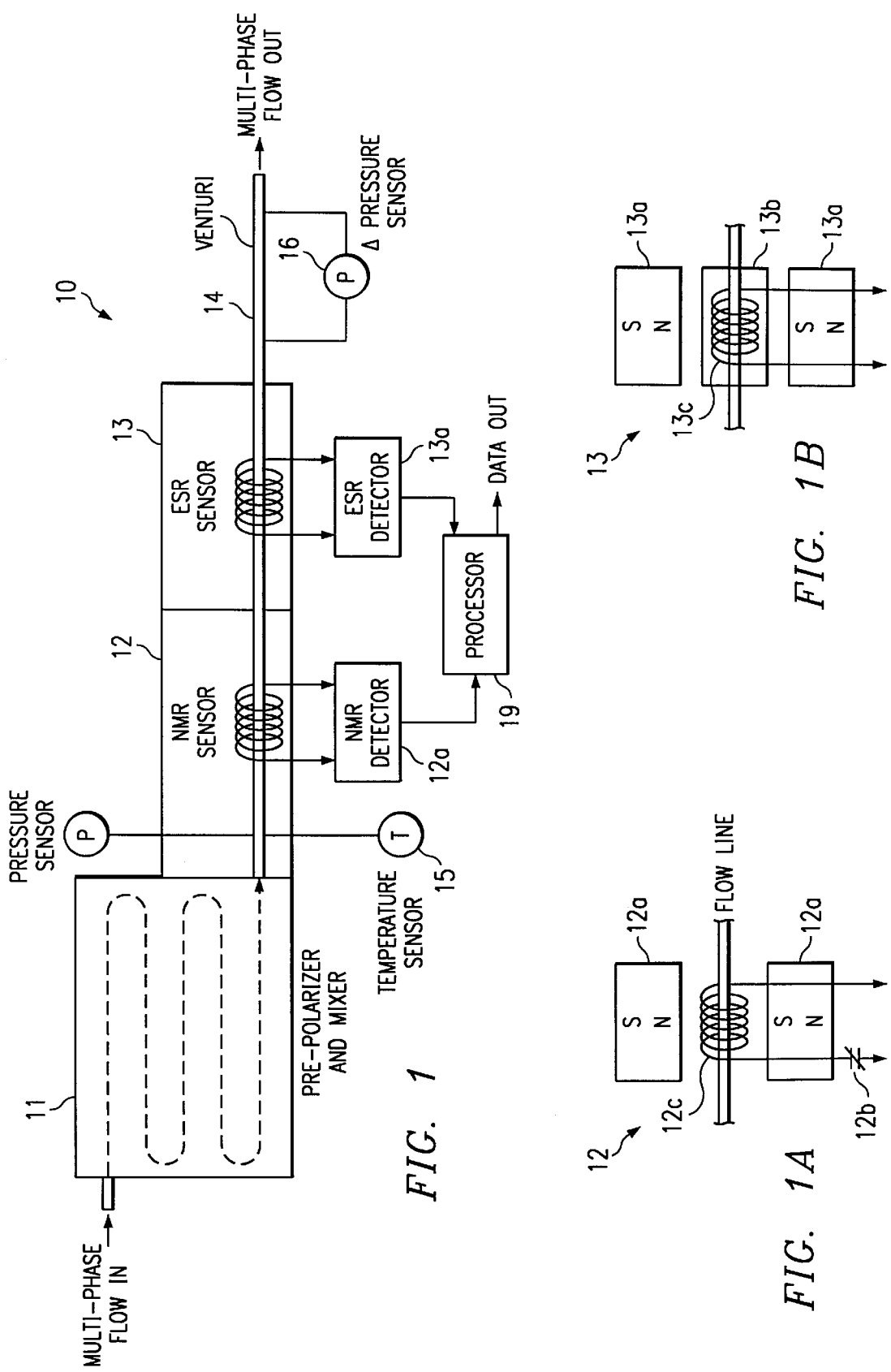

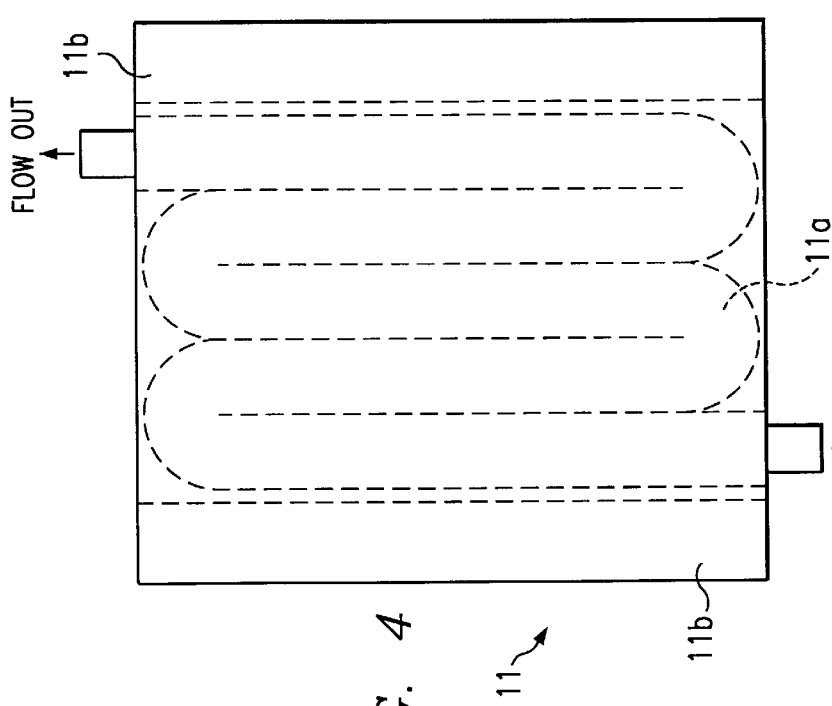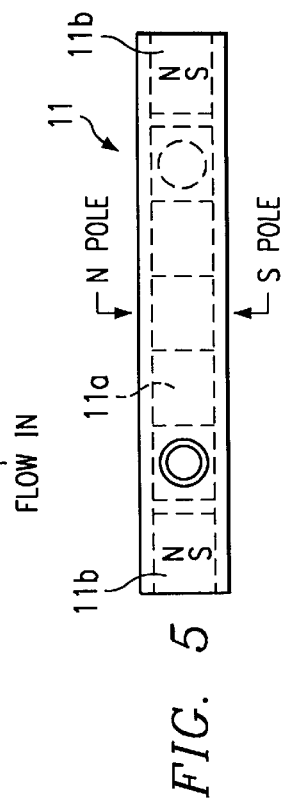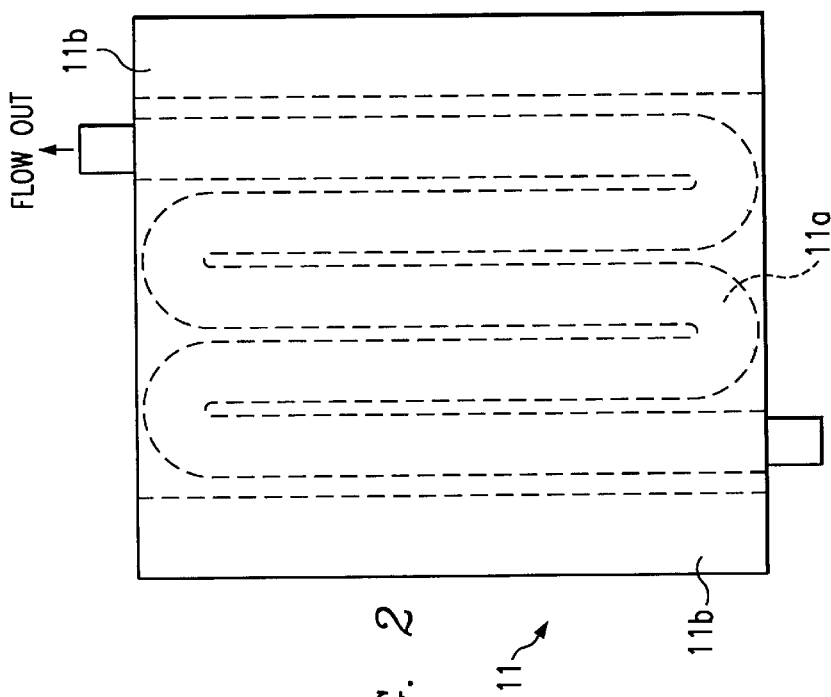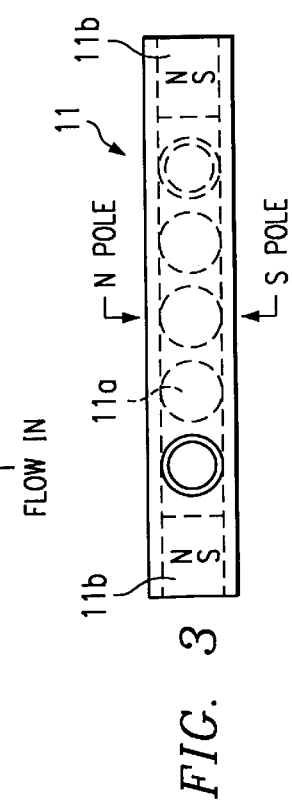

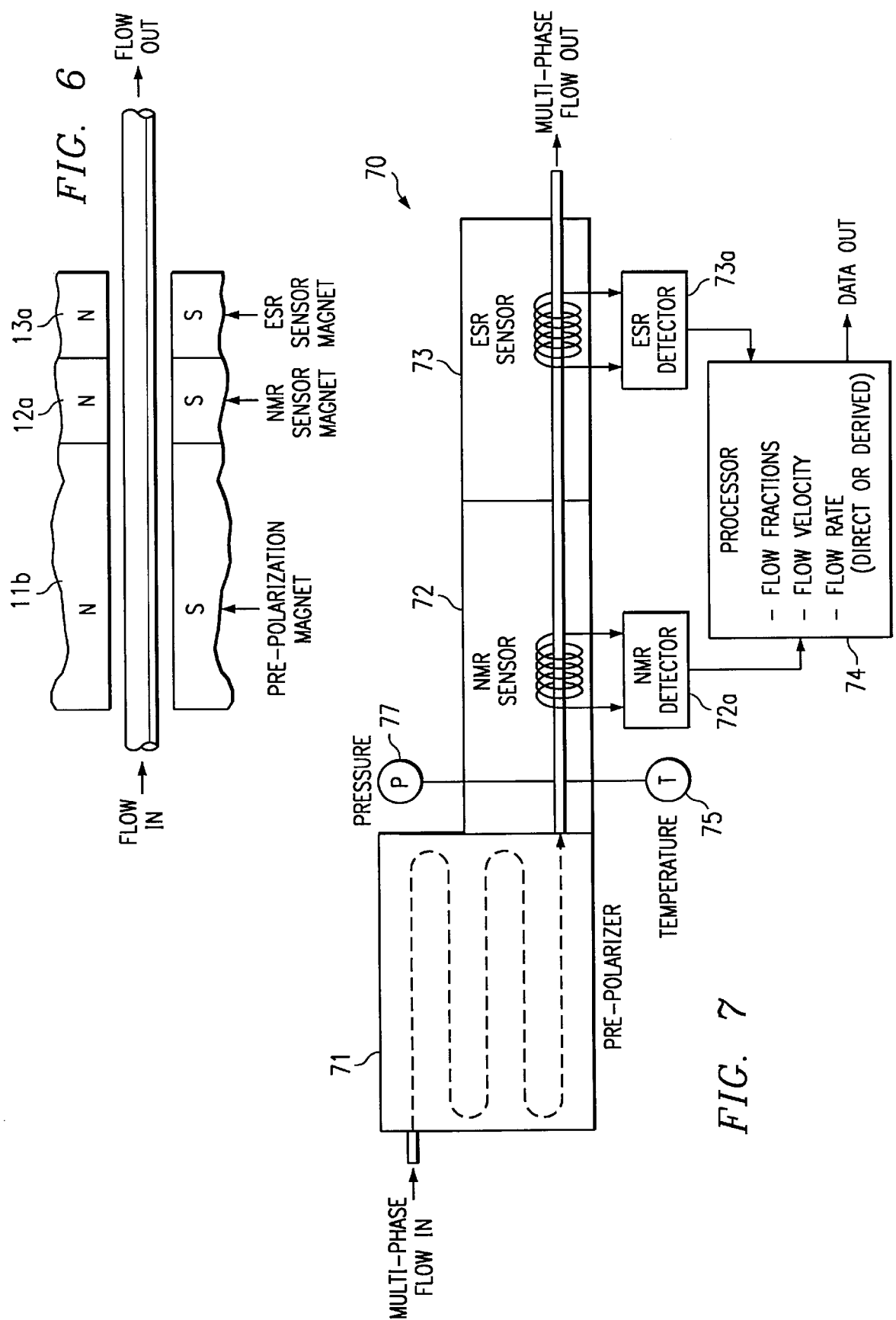

MEASUREMENT OF FLOW FRACTIONS FLOW VELOCITIES AND FLOW RATES OF A MULTIPHASE FLUID USING ESR SENSING

RELATED PATENT APPLICATION

This application claims the benefit of U.S. Provisional Application No. 60/050,637, filed Jun. 24, 1997 and entitled "Measurement of Separate Flow Fractions and Flow Rates of a Multiphase Fluid."

TECHNICAL FIELD OF THE INVENTION

The present invention relates generally to instruments for metering multiphase fluids, that is, measuring the separate percentages of gas and liquid (or separate liquids such as oil and water) in such fluids as well as the velocity and rate of the mixed fluid or the separate liquid and gas velocities and rates.

BACKGROUND OF THE INVENTION

A "flowmeter" is a device used to measure the flow of fluid material through a defined area, such as the cross sectional area of a pipeline. The "flow" is the motion of the fluid, which may be liquid or gas or a combination of both. The flowmeter measures the flow in terms of the flow rate, the amount of the fluid that flows over a given period.

There are various ways to express flow rate, such as by mass flow rate, volumetric flow rate, or velocity of flow. Mass flow rate is the flow rate in units of mass per unit time, i.e., kilograms per second. Volumetric flow rate is the flow rate in units of volume per unit time, i.e., cubic meters per second. Velocity of flow is in units of length per unit time, i.e., meters per second.

Most measurements of flow are in terms of volumetric flow rate. Mass flow rate can be calculated from this measurement, although variations in pressure, density, temperature must be taken into account, particularly for gases. Similarly, a measurement of velocity of flow can be used to calculate mass or volumetric flow rate.

Conventional flowmeters are designed for single phase fluids, that is, fluids that are either gas or liquid. Some existing flowmeters are mechanical, where the flowing fluid displaces or rotates a solid body. The displacement or rotation is proportional to the flow rate. Another type of flowmeter is a differential pressure flowmeter, in which fluid is forced through some type of restricted area. This causes its velocity to change, causing a pressure difference that is proportional to flow. By measuring the pressure difference, such as with a differential pressure transducer, the flow rate can be determined. Other flowmeter types are thermal, electromagnetic, vortex generating, and ultrasonic. The criolis force flowmeter is widely used for measuring mass flow.

When the fluid whose flow rate is to be measured is a multiphase fluid, special problems arise. An example of such a fluid is a hydrocarbon fluid, which is typically a mixture of oil and gas as well as water. For a multiphase fluid, there is often a need to know the liquid and gas "cuts", that is, the fractional amount of each constituent at a given point in a flowline, as well as their rates. In the case of petroleum fluids, there is a need to know the oil cut as distinguished from both the water and gas cuts.

One consideration when measuring the flow rate of multiphase liquids is that the gas component tends to flow at a higher velocity than the liquid component. It is therefore necessary to separately measure the gas and liquid flow velocities or to measure the total flow velocity after mixing the fluid.

An additional consideration in measuring a multiphase fluid is that the density of the gas, except at very high pressures, is low compared to that of the liquid. This makes direct measurement of the gas fraction difficult. Typically, the liquid fraction is measured and the remainder is assumed to be gas. In other words, if a pipe section is half filled with liquid, then the other half is assumed to be gas.

The conventional approach to measuring multiphase flow rates is to separate the fluid into its constituents. This permits conventional single phase metering techniques. However, especially in the petroleum industry, as the water and gas content of recoverable petroleum has increased and oil fields have become more inaccessible, there is a need for more sophisticated multiphase flowmetering equipment.

Several patents have been issued that describe the use of nuclear magnetic resonance (NMR) analysis to analyze fluid flows that are not necessarily multiphase. These include U.S. Pat. No. 4,531,093, to Rollwitz, et al., entitled "Method and Apparatus for Coal Analysis and Flow Measurement"; U.S. Pat. No. 4,536,711, to King, et al., entitled "Method and Apparatus for Measuring Flow in a Pipe or Conduit"; and U.S. Pat. No. 4,866,385, to Reichwein, entitled "Consistency Measuring Device".

NMR techniques have been specifically applied to analyzing multiphase fluids. U.S. Pat. No. 4,785,245, entitled "Rapid Pulse NMR Cut Meter," describes a flowmeter that uses NMR analysis to determine the fraction of one component of a multiphase fluid flowing in a pipeline. The amplitude of the NMR signal from a desired component is compared to a reference signal representing a 100% sample of the component.

SUMMARY OF THE INVENTION

One aspect of the invention is a flowmeter having both a nuclear magnetic resonance (NMR) sensor and an electron spin resonance (ESR) sensor. This flowmeter can be used to determine a variety of fluid flow parameters. The ESR output data is used to determine the fraction of liquid petroleum, such as crude oil, that exhibits a favorable ESR characteristic. The NMR output data can be used to determine total density of all fractions that exhibit favorable NMR characteristics. Combined with temperature and pressure data, it can be used to determine the gas and liquid fractions. If the flowmeter has a mixer, total flow velocity can be measured with a venturi. Without a venturi, velocity can be determined from NMR data, using a "variable delay" pulse sequence. Alternatively, the fluid can be measured by NMR in a gradient field, and a frequency spectrum analysis used to determine separate liquid and gas velocities. The NMR output data can also be used to directly determine flow rates. The gradient field method can also be used with ESR data to determine the velocity of liquids that exhibit favorable ESR characteristics.

An advantage of the invention is that each fraction of a multi-phase fluid can determined. Depending on which of the various techniques are used, total or separate flow velocities can be measured, as well as the flow density and the totalized flow rate. The invention is especially useful for fluids containing gas, oil, and water because the flow rates of any two or all three of these constituents can be determined.

The sensor equipment can be located remotely from the detection electronics and processing equipment. The results are available in real time as the fluid is flowing in situ.

BRIEF DESCRIPTION OF THE DRAWINGS

FIG. 1 illustrates a flowmeter having an NMR sensor and ESR sensor for measuring flow fractions and a venturi for measuring flow velocity.

FIGS. 1A and 1B illustrate the NMR sensor and ESR sensor, respectively, of FIG. 1.

FIGS. 2–5 illustrate two embodiments of the pre-polarizer of FIG. 1.

FIG. 6 illustrates the magnetic field configuration provided by the pre-polarizer and the NMR and ESR sensors of FIG. 1.

FIG. 7 illustrates a flowmeter having an NMR sensor and ESR sensor for measuring flow fractions and flow velocity.

DETAILED DESCRIPTION OF THE INVENTION

Figure 8A:
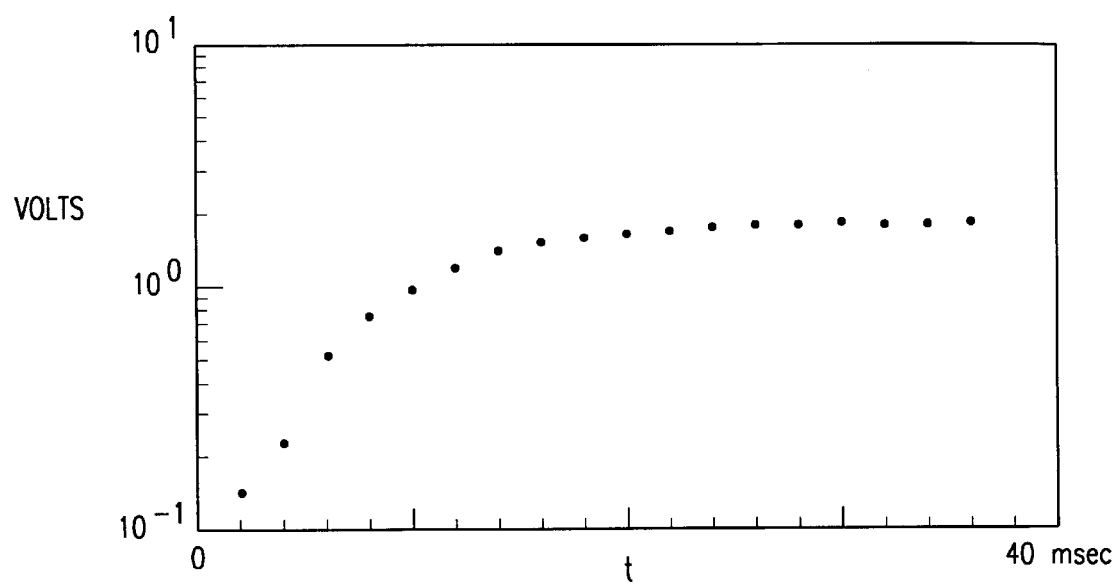
FIGS. 8A and 8B illustrate how velocity may be measured using the NMR sensor of FIG. 7.

The following description describes several different flowmeters, each of which provides NMR (nuclear magnetic resonance) or ESR (electronic spin resonance) signals. In some cases, the flowmeter provides both types of signals. ESR is sometimes referred to as EPR (electron paramagnetic resonance). ESR is similar in its principal of operation to NMR but unpaired electrons (due to free radicals, broken bonds, and paramagnetic elements) in materials are detected instead of the nuclei of the hydrogen atom.

The flowmeters analyze these signals to derive the fractional amounts of liquid and gas (or fractional amounts of oil, water, and gas) in a multiphase fluid. Various methods of using these flowmeters to also derive flow velocity are also described. The flow velocity may be of a mixed fluid, where the gas and liquid flow at the same velocity, or of separate velocities of the gas and liquid. Methods of deriving total and fractional flow rates are also described.

In the examples of this description, the multiphase fluid is measured as it is transported in a pipeline. However, the flowmeters described herein can be used in conjunction with other fluid transport means such as a conveyor belt, an open trough, a vertical flow under the force of gravity, or by any other transport means that moves the fluid through space as a function of time.

For purposes of example, the multiphase fluid is assumed to be a combination of hydrocarbon gas and oil as well as water. Thus, the fluid has two liquid constituents (oil and water) and a gas constituent. Various flowmeters described herein are capable of measuring the fraction of each constituent. However, the flowmeters are useful for other multiphase fluids, with another example being a gas that is partially liquefied. The invention can also be used with single phase liquids or gases.

For NMR sensing, the nuclei to be detected are those of hydrogen. These nuclei are present in water, oil, and hydrocarbon gases, and provide better NMR measurement sensitivity than other types of atomic nuclei.

Flowmeter with NMR Sensor. ESR Sensor, Fractional Analysis, and Venturi Velocity Measurement FIG. 1 illustrates a first embodiment of the invention, an NMR/ESR flowmeter 10, which measures fractional amounts of liquid and gas in a multiphase fluid. In the example of this description, the fluid contains water, oil, and gas. As explained below, flowmeter 10 uses both NMR (nuclear magnetic resonance) and ESR (electronic spin resonance) analysis.

The fluid material passes through a pre-polarizer 11, which is essentially a magnet that polarizes the magnetic moments of both nuclei and free or un-paired electrons that are present in the fluid. Such pre-polarization provides rapid and sensitive detection of NMR signals from a flowing material, especially from materials that have a long polarization time, i.e., long $T_1$ materials. For ESR, extended length pre-polarization is not needed.

The amount of polarization provided by pre-polarizer 11 depends on whether NMR or ESR sensing is being performed, on the properties of the fluid, and on the flow velocity. For a given fluid, the polarization time is a certain time constant. For ESR signals, the polarization time my be less than a microsecond. For NMR signals, the polarization time may be as much as several seconds or more.

For NMR sensing, the polarization time constant, $T_1$, is the spin-lattice relaxation time. For hydrogen nuclei (protons) in water, $T_1$ is in a range of 2.0 to 2.5 seconds. An exception is if the water is contaminated with paramagnetic ions. For crude oil, $T_1$ varies with temperature but typically has two values, one in the range of 0.05 to 0.15 seconds and one in the range of 0.4 to 0.9 seconds. These are due to the different molecular constituents and the oils may have more than two values of $T_1$. For hydrocarbon gases, $T_1$ varies with temperature, pressure, and the type of gas. For hydrogen gas, $T_1$ can be quite short, from 10's to 100's of microseconds. For methane, $T_1$ is from 10's to 100's of milliseconds at typical land pipeline temperatures and pressures, and is up to a few seconds at subsea temperatures and pressures. For heavier hydrocarbon gases, $T_1$ typically ranges from hundreds of milliseconds to several seconds.

The degree of magnetic polarization, $M_p$, prior to measurement of the NMR and ESR signals determines the amplitude of these signals. For a simple material, the magnetic polarization may be expressed as $$M_p = M_0 \left(1 - e^{-\frac{t}{T_1}}\right), \quad (1)$$

where $M_0$ is the maximum polarization in a magnetic field of strength $H_0$, t is the time the material is exposed to $H_0$, and $T_1$ is the spin-lattice relaxation time constant. The polarization time, t, is equal to the length of the pre-polarization magnet divided by the flow velocity.

As examples of the above calculation of the magnetic polarization, for $t=T_1$ then $M_p=0.632\ M_0$, and the detected NMR signal amplitude is 36.78% lower than the maximum that would be attained if $t>>T_1$. For $M_p=0.9\ M_0$ then $t=2.3\ T_1$, for 0.95 then $t=3T_1$ and for 0.99 then $t=4.6\ T_1$. For NMR measurements, the amplitude of the NMR signal from material of a given type and concentration is preferably substantially constant despite changes in flow velocity. To this end, the length of the polarization magnet should be such that the polarization times at the highest velocity and at the lowest velocity are in accordance with an allowable variation in $M_p/M_0$ as determined by Equation (1). The invention achieves this goal with a compact and cost effective design. Alternatively, if velocity is known, flowmeter 10 can provide less than full polarization and compensation can be made for the effect of velocity changes on the NMR signal amplitude.

FIGS. 1A and 1B illustrate the NMR sensor 12 and ESR sensor 13, respectively, of FIG. 1. NMR sensor 12 and ESR sensor 13 each have a magnet 12a and 13a, which provides an Ho field through the flow pipe in the sensor 12 and 13, and a sensor coil 12c and 13c. Each also has a tuning element (which could be a resonant cavity), that is tuned to the NMR or ESR frequency, as appropriate, illustrated as a tuned capacitor 12b for NMR sensor 12 and a resonator or tuned coil 13b for ESR sensor 13. The flow conduits through sensors 12 and 13 are of non-conductive material to permit passage of the RF fields from the sensor coil 12c and 13c (or cavity or other resonator) to the flowing fluid.

FIGS. 2–5 illustrate two different embodiments of pre-polarizer 11 using permanent pre-polarizer magnets 11b. FIGS. 2 and 3 are a plan view and a cross sectional view of a pre-polarizer 11 having a round flow channel 11a. FIGS. 4 and 5 are a plan view and a cross sectional view of a pre-polarizer 11 having a rectangular flow channel 11a. In both embodiments, the flow channel 11a is folded in a single plane between two steel or iron plates, which are the pole pieces of the magnet. Permanent magnets 11b are located along both sides of the plane to provide the magnetic field to the pole pieces. The conduit could also be on parallel planes between these pole pieces. These embodiments of pre-polarizer 11 are designed to provide optimum polarization with a given amount of magnetic energy and to minimize the size of pre-polarizer 11. A conventional straight flow conduit between the poles of a polarizing magnet or a spiral flow conduit between the poles of a polarizing magnet could also be used. The flow conduit 11a in the pre-polarizer is of non-ferromagnetic material that permits external magnetic fields to penetrate through the flowing fluid.

FIG. 6 illustrates the magnetic fields provided by pre-polarizer 11 as well as by the sensor magnets in the NMR sensor 12 and ESR sensor 13. Separate sensor magnets of different Ho values can be used in the NMR and ESR sensors. The flow channel is transverse between the magnet poles, N and S. A magnet based on a Watson configuration, as illustrated in FIGS. 2–5, is especially suitable although other magnet designs can be used.

Referring again to FIG. 1, pre-polarizer 11 incorporates features to provide uniform mixing of the gas and liquid within the fluid. This results in a single flow velocity for the mixed fluid, which is measured with venturi 14.

After polarization, NMR sensor 12 is used to detect the NMR signal. NMR sensor 12 is comprised of a magnet, which provides a static field of intensity, $H_0$, and a radio frequency (RF) coil, L, which is tuned by capacitance to the NMR (Larmor) frequency, $f_0$. This coil encircles (or is in close proximity to) the flowing fluid and produces an RF magnetic field that is oriented normal to the static field, $H_0$. The NMR frequency is given by $$f_0 = \gamma H_0 \text{ MHz}, \quad (2)$$

where $H_0$ is in Tesla and $\gamma$ is the gyromagnetic moment of the nuclei under observation. For hydrogen, this frequency is approximately $42.6 H_0$ MHZ. The ESR sensor 13 used to detect ESR signals from crude oil and other ESR-favorable materials is comprised of a magnet that provides a static field of intensity Ho and a coil or cavity resonator tuned to the ESR frequency.

NMR sensor 12 and ESR sensor 13 are each in communication with an associated detector 12a and 13a, respectively. Detectors 12a or 13a are each comprised of a signal generator for energizing the sensor coil, or resonator, at the NMR or ESR frequency, as well as electronic circuitry for receiving, amplifying, and detecting an output signal from the sensor and delivering the output signal to processor 19. For simplicity of description, the combination of a sensor and detector for NMR or ESR is sometimes referred to herein as simply a "sensor". However, an advantage of the invention is that the sensor (comprised of the tuned coil and the sensor magnet) and the detector may be separate and remote from each other.

According to NMR theory, the polarized fluid will emit an RF electromagnetic field oscillating at the NMR (Larmor) frequency when energized by a pulse (such as a 90 degree pulse) of RF electromagnetic field of the NMR (Larmor) frequency. When the NMR sensor coil is energized by a multiplicity of such RF pulses, nuclei in the fluids being measured produce sinusoidal electrical signals at the NMR frequency in the sensor coil as one or more RF pulses. The duty period of the pulses and the delay between pulses may be controlled by the sensor's electronic circuitry to maximize a desired NMR response.

For one use of the embodiment of FIG. 1, a single pulse may be used to energize the sensor coil. The NMR output signal is a transient free induction decay (FID) signal from the hydrogen nuclei. For maximum amplitude of the FID signal, the nuclei should be fully pre-polarized prior to the pulse and the pulse energy should be such as to deflect the nuclei by an angle of 90° from alignment with the static field, $H_0$. A pulse that deflects the nuclei in this manner is referred to as a "90° pulse". However, useful NMR FID signals may be obtained with less than full polarization and with a pulse that is shorter than 90°.

The peak amplitude of the FID signal is proportional to the total number of hydrogen nuclei in the coil of NMR sensor 12, to the amount of polarization, $M_p$, and to the energy of the RF pulse. Using NMR analysis techniques, the total hydrogen density of the fluid can be calculated. For a fluid containing oil, water, and gas, this total represents the contribution of each constituent.

Processor 19 is programmed to calculate total hydrogen density of the fluid from the FID signal data. It has associated memory for storing the programming, calibration factors, and data used for such calculations. It may also be programmed to perform various other calculations described below, such as the separate fractions for gas, water, and oil, as well as total velocity and flow rates of the fluid.

The NMR measurement of the total hydrogen density, together with pressure and temperature measurements from sensors 15 and 17, can be used to determine the gas fraction in the fluid. Specifically, if the sensor coil were to contain only liquid, the FID signal would have a known maximum amplitude value. This value decreases with the presence of gas. Thus, the gas fraction may be calculated as a function of the FID signal amplitude and the fluid pressure and temperature.

ESR sensor 13 measures the fraction of crude oil in the fluid (the "oil cut"). Because of the short polarization time for ESR signals, ESR sensor 13 need only be a few centimeters long. For ESR signals, the frequency, $f_0$, is approximately $28 H_0$ GHZ. Thus, for a given magnetic field, ESR resonances are much higher in frequency than NMR resonances and the ESR sensitivity is greater.

ESR sensor 13 senses unpaired electrons, which are present in most crude oils, that is, petroleum liquid prior to refining. No ESR signal is produced by water or gas. The ESR signal amplitude is proportional to the density of the unpaired electrons, and thus to the amount of oil in a pipe cross section. Thus, by using ESR to sense the oil in a multiphase flow, a separate and direct measurement of the crude oil fraction can be obtained. Although not all crude oils have the same signal amplitude for a given concentration, calibration factors for the type of oil can be readily derived and applied. In addition, certain ESR signal features in crude oils can provide the basis for identifying certain crude oils or detecting particular constituents.

Once the oil fraction and gas fraction are known, using the methods described above, the remainder of the fluid can be assumed to be water. Alternatively, the water fraction can be determined by the NMR sensor as described below.

In sum, in the case of flowmeter 10, NMR sensor 12 is used to determine the total fluid density. ESR sensor 13 is used to determine the oil fraction. A mixer is incorporated in pre-polarizer 11 to insure a homogeneous mixture of gas and liquid that flows at a single velocity. The total flow velocity is measured in venturi 14 using differential pressure, total pressure, and temperature measurements. FIG. 1 illustrates suitable locations for a temperature sensor 15, pressure sensor 16, and differential pressure sensor 17.

Flowmeter with NMR Sensor, ESR Sensor, Fractional Analysis, and NMR Velocity Analysis FIG. 7 illustrates an alternative embodiment of the invention, a flowmeter 70 where the fluid is not mixed and a venturi is not used. Flowmeter 70 has a pre-polarizer 71, NMR sensor 72, ESR sensor 73, and temperature and pressure sensors 75 and 77. Each of these components operates in a manner similar to the corresponding components of flowmeter 10.

For determining liquid and gas fractions, flowmeter 70 may be programmed and used in the manner described above for flowmeter 10. Specifically, NMR sensor 72 and ESR sensor 73 may be used to provide signals that are analyzed by processor 74 to determine separate oil, water, and gas fractions.

Flow velocity is obtained using NMR sensor 72, energized by the following "variable delay" pulse sequence:

$$p_1-\tau-p_2-\text{acquisition}-d,$$

where $\tau$ is a variable delay between pulses. It is assumed that a length of the pipe line, $X_1$ carrying the fluid prior to entry into NMR sensor 72 is immersed in a static magnetic field to pre-polarize the nuclei, such as is accomplished with pre-polarizer 71. The length of the pipe line inside the NMR sensor coil is $X_0$, where $X_1 >> X_0$. If the fluid is a liquid (perhaps an oil-water mixture) flowing at velocity, v, then the delay time, $\tau$, is started at 1 millisecond and increased to a value that is longer than $X_0/v$. It is also assumed that the static magnetic field is in the z direction so that all the proton nuclear magnetization are aligned or partially aligned along the z direction before entering the coil of NMR sensor 72.

For velocity measurement, the FID signal is observed immediately after the first 90 degree RF pulse, $p_1$. Under these conditions, the FID signal amplitude may be modeled as follows:

$$F = M_0 dSX_0(1-e^{(-X_1/vT_1)})f, \quad (3)$$

where S is the cross sectional area of the pipe, d is the density of the protons (nuclei of the hydrogen atoms in the water and oil), $T_1$ is the spin-lattice relaxation time, $M_0$ is the maximum nuclei polarization, and f is a calibration factor.

After the delay time, $\tau$, and after the second 90 degree pulse, $p_2$, the FID signal is:

$$F(\tau) = M_0 dS(X_0 - v\tau)(1-e^{-X_1/vT_1})(1-e^{-\tau/vT_1}) + M_0 dSv\tau(1-e^{-X_1/vT_1}), \quad (4)$$

where dSvt represents the segment of fluid entering and exiting from the inlet and outlet of the coil during time $\tau$.

If the delay time $\tau$ equals or exceeds $X_0/v$, then all the material in the coil will contain "fresh protons" and the FID signal is at a maximum. "Fresh protons" are those that are polarized and not previously exposed to an RF pulse of the NMR frequency. Such exposure reduces the effective polarization, which results in a smaller FID signal following a second pulse of the same material.

Figure 8B:
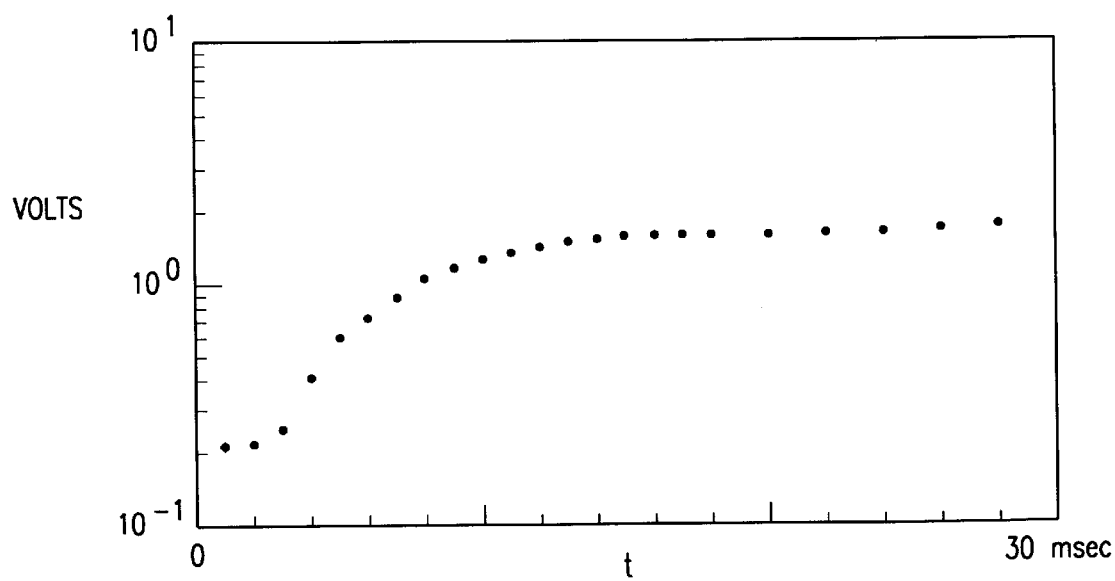

FIGS. 8A and 8B each represent a series of measurements, where $\tau$ (the time delay between a first pulse and a second pulse) is varied to increase in increments of 2 milliseconds. In FIG. 8A, the FID signal amplitude reaches a maximum value at $\tau = 26$ milliseconds. This indicates a flow velocity of 1.46 meters per second for a 3.81 cm (1.5 inch) long sample coil. In FIG. 8B, the FID signal amplitude reaches a maximum value at $\tau = 15$ milliseconds. This indicates a flow velocity of 2.54 meters per second for a 3.81 cm long sample coil.

For a given fluid, the velocity, v, can be determined by the FID amplitude at two values of $\tau$. Using Equation (5), two values of $F(\tau)$ are obtained. One value of $\tau$ is the value representing the maximum signal, where $\tau \geq X_0/v$, where v is a maximum expected velocity, and thus the coil of NMR sensor 72 can be assumed to be full of fresh fully polarized protons. Another value of $\tau$ is at a point where the coil is less than full of fresh protons. The faster the velocity, the larger will be the second FID amplitude relative to the first. The two equations, each representing a different value of $F(\tau)$, can be solved for v. A feature of this method of determining velocity, is that measurements need be made at only a single location in the pipeline.

For velocity analysis, fluid mixing is optional. Typically, the NMR signal from the liquid fraction(s) is much stronger than that of the gas fraction. Thus, for unmixed fluids, the NMR analysis will substantially reflect the liquid velocity. Instead of mixing, it may be more desirable to maximize either the stratified or annular flow of the gas and liquid for the velocity measurements. Thus, pre-polarizer 11 may incorporate means to enhance either mixing (for total flow velocity) or stratification (for liquid flow velocity). If the fluid is gas only, the gas signal will be detectable and the above-described method can be used to determine the gas velocity.

Direct Measurement of Flow Rates

Liquid flow rates can be directly determined with NMR signal measurements. This method uses the following pulse sequence:

$$p_1-\text{acquisition}-\tau-p_1\text{acquisition}-\tau-\text{acquisition}-\tau-p_1-\text{acquisition},\ldots,$$

where $p_1$ is a 90° pulse, $\tau$ is the delay time between pulses, and "acquisition" is the time interval during which the FID NMR data is acquired from the flowing fluid. In essence, this method measures the new polarized material that enters the NMR sensor coil between pulses. The delay time, $\tau$, is selected to be no longer than the fluid transit time through the NMR sensor coil at the highest expected velocity, with compensation for the signal acquisition time. Under these conditions, the amplitude of the NMR FID signal, F, may be expressed as:

$$F = \rho vf - g,$$

where $\rho$ is the density (as measured by the hydrogen concentration in the fluids), v is the flow velocity, f is a calibration factor, and g is a factor to compensate for any residual polarization in the flowing material following the pulse, $p_1$. Thus, the FID signal amplitude represents a direct function of the flow rate.

For a given density, the output signal amplitude has a maximum value when the sensor coil is completely full of fresh fluid at a maximum velocity. For a lower flow velocity, the sensor coil contains old (previously measured) material as well as some new polarized material, and the signal amplitude is lower.

Thus, for direct measurement of flow rate, a first output signal is acquired when the sensor coil is known to be full of fresh fluid. This signal represents the maximum for that fluid. After the time delay, τ, a second output signal is acquired. Its amplitude relative to the first indicates the flow rate. For example, if a fluid flowing at the highest expected velocity refills the coil during a reference delay time, τ, a series of signals acquired after pulses with this delay time (with compensation for the signal acquisition time) will be substantially constant in amplitude, A. If the same fluid of unknown velocity has an output signal of only A/2 after the same reference delay time, it is known that its velocity and therefore its flow rate are only half that of the first. Flow rate could also be determined by taking measurements at varying values of τ, determining which value of τ produced a substantially constant output signal, and comparing this value of τ with that of the reference.

This method of directly measuring flow rate, used with a mixed fluid, such as the mixed fluid of flowmeter 10, provides a total flow rate. If the fluid is not mixed, the method can be used with flowmeters 70 or 90 to provide a separate flow rate for the liquid constituents.

Flowmeter with Dual NMR Sensors

Figure 9:
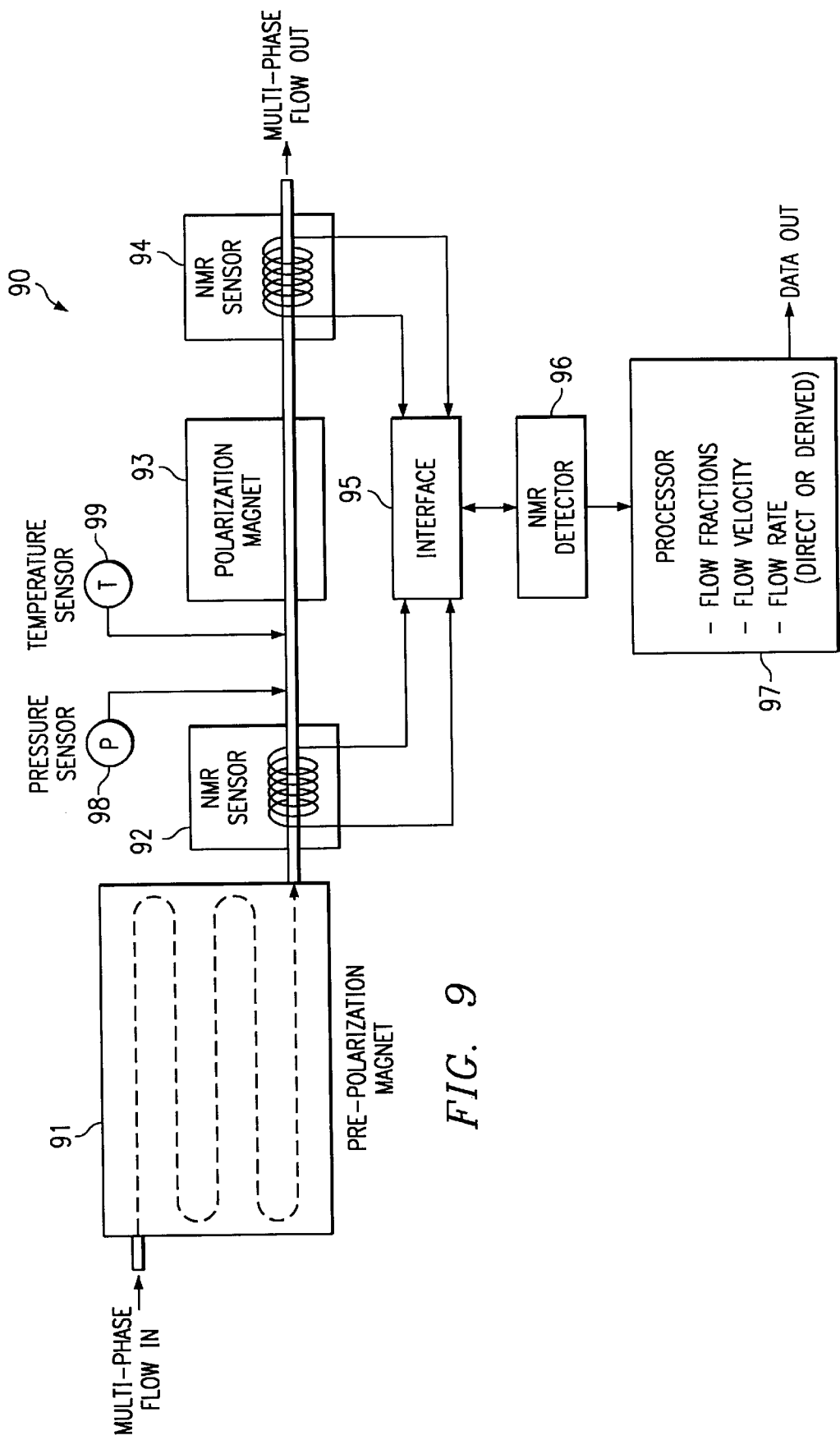
FIG. 9 illustrates a flowmeter that uses two NMR sensors for measuring flow fractions.

FIG. 9 illustrates a flowmeter 90 that uses two pre-polarizers and thus two pre-polarization intervals. A first pre-polarizer 91 pre-polarizes the fluid, and a first NMR sensor 92 measures the FID amplitude after this first polarization. A second pre-polarizer 93 is shorter than the first pre-polarizer 91 and partially pre-polarizes the fluid. A second NMR sensor 94 again measures the FID amplitude. In one embodiment, the first and second NMR sensors and the second pre-polarizer make use of a single, common magnet that extends over the two sensor coils and over the separation distance between these coils.

From the two FID amplitude measurements, the separate fractional amounts of the two liquid components (oil and water) can be determined. Specifically, if the lengths of the first and second pre-polarization flow channels are X1 and X2, respectively, the FID signals, F1 and F2, may be expressed as:

$$F1 = M_0 f d_w X_0 (1-\exp(-X_1/vT_{1w})) + M_0 f d_{oil} X_0 (1-\exp(-X_1/vT_{1oil})) \quad (5)$$

$$F1 = M_0 f d_w X_0 (1-\exp(-X_2/vT_{1w})) + M_0 f d_{oil} X_0 (1-\exp(-X_2 vT_{1oil})), \quad (6)$$

where $d_w$ and $d_{oil}$ are the densities for water and oil, $T_{1w}$ and $T_{1\ oil}$ are the spin-lattice relaxation time for water and oil, respectively, $M_0$ is the maximum polarization, and f is the calibration factor.

Values of $T_{1w}$ and $T_{1\ oil}$ can be obtained by measurements of the mixture of oil and water and used as calibration factors. The following table set out $T_{1\ oil}$ values for several crude oils. Two $T_1$ values are present and these values range from about 0.464 to 0.862 seconds for the longer components and from about 0.077 to 0.114 seconds for the shorter components.

| | Crude Oil Samples | | | | | | |
|---|---|---|---|---|---|---|---|
| $T_1$ (ms) | A | B | C | Da | Ta | Lan | Do |
| *$T_{11}$ (ms) | 489 | 795 | 558 | 477 | 862 | 479 | 464 |
| *$T_{12}$ (ms) | 77 | 101 | 114 | 101 | 124 | 93 | 92 |

*$T_{11}$ and $T_{12}$ are longer and shorter components of $T_1$, respectively.

The $T_{1w}$ value for water is typically about 2.2 seconds, though it can be much lower if the water contains paramagnetic ions. Equations (5) and (6) can be solved for $d_w$ and $d_{oil}$, and hence used to derive fractional amounts of water and oil.

The gas fraction may be determined in a manner similar to that described above for flowmeter 10. For flowmeter 90, this method uses the total FID amplitude from the first NMR sensor 92 together with pressure and temperature measurements from sensors 97 and 98.

Fluid velocity can be determined using NMR sensor 92 and a pulse sequence and the method described above for flowmeter 70. As stated above, the fluid velocity measurement approximates the liquid velocity. If liquid fractions and liquid velocity are known, separate flow rates for the water and oil can be calculated. The flow rate, r, is the product of density and velocity.

One of the magnets of sensor 92 or 93 may provide a gradient field for determining separate flow velocities as described below in connection with FIG. 10.

Separate Flow Velocities From Gradient Field

Figure 10:
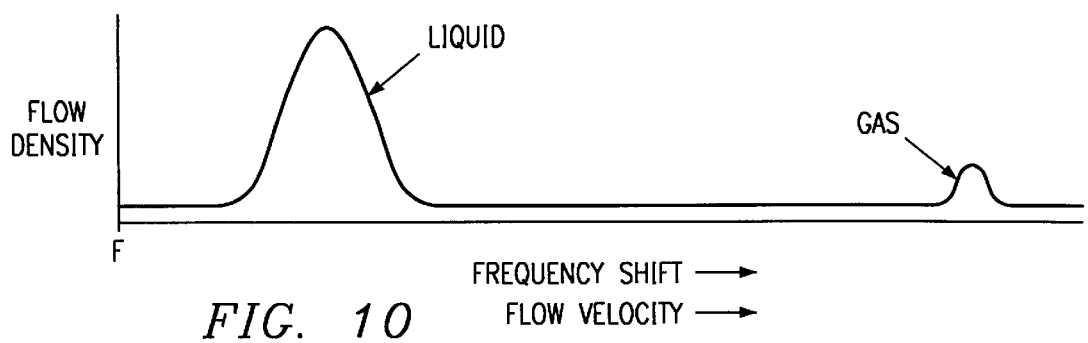
FIG. 10 illustrates how a gradient polarization field and an NMR sensor may be used to determine separate liquid and gas flow velocities.

FIG. 10 illustrates a method of measuring separate flow velocities for gas and liquid. This method involves using a pre-polarizer followed by a sensor magnet, which provides a gradient magnetic field in the sensor. For example, for the flowmeter 10 of FIG. 1, the magnet in sensor 12 may be used in this manner. Although the following description is in terms of NMR sensing, the same concepts can be used for ESR sensing.

U.S. Pat. No. 4,536,711, to King and Riewarts, entitled "Method and Apparatus for Measuring Flow in a Pipe or Conduit", and incorporated herein by reference, describes a method of using NMR or ESR sensing and a gradient magnetic field to measure flow velocity. As a segment of flowing fluid moves through the gradient field, the frequency of the NMR signal from the fluid changes. If the field gradient is linear, the frequency change is linear. The frequency change at a time, τ, following an NMR excitation pulse, p, and is proportional to the velocity of the fluid. For example, a fluid having velocity, v, will have a frequency shift through the gradient field at time τ that is half that of a fluid having a velocity of 2v.

For gradient field velocity measurements, a pulse sequence appropriate for acquiring a Hahn echo NMR signal may be used. An FID signal may also be used to acquire velocity data.

As illustrated in FIG. 10, by using a fast Fourier transform, the NMR signal data may be represented as a function of frequency. If the NMR signal is from fluid flowing in a gradient field, the frequency spectra reflects the flow velocity. For example, if the magnetic gradient causes a shift of 1.0 khz in the frequency of the NMR signal from liquids moving at 5 meters per second, then the NMR signal from gas moving at 25 meters per second would be centered on a frequency shift of 5 khz. Although the gas signal is typically of lower amplitude than the liquid signal, with sufficient resolution, each of these signals can be separately detected and measured. The frequency shift provides the flow velocity while the area under the spectra peak provides the flow density in terms of hydrogen nuclei.

For gradient field measurements, stratified or annular flows are preferable, and the flowmeter may contain means for enhancing these type of flow. The amplitude of each spectral component is proportional to the concentration of nuclei in an associated liquid or gas constituent flowing at the same velocity. The frequency location indicates the flow velocity. The separation between spectral components permits the higher flow velocity gas signal to be detected separately from that of the slower liquid.

The gradient field method is applicable to ESR output signals, except that the amplitudes represent the density of unpaired electrons rather than nuclei. Also, the ESR signal would be produced only by a crude oil constituent, or other constituent with favorable ESR properties, and the velocity would reflect total velocity if the fluid is mixed and liquid velocity if the fluid is not mixed.

Flowmeter with ESR Sensor

Figure 11:
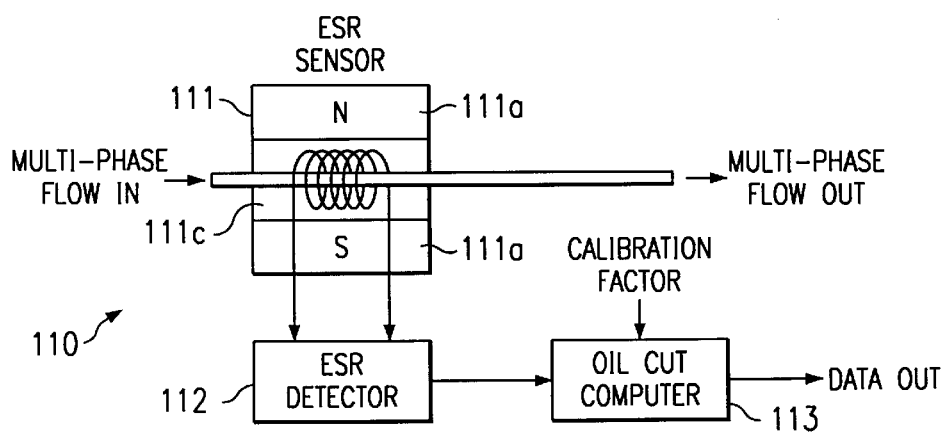
FIG. 11 illustrates a flowmeter having only an ESR sensor for measuring an oil fraction and oil velocity.

FIG. 11 illustrates an ESR flowmeter 110, where ESR signals are used to measure the oil cut in a flowing fluid. The detected ESR signal amplitude, multiplied by a calibration factor for the apparatus and for the type of oil, provides a measure of the oil fraction.

A ESR sensor 111 (composed of a magnet 111a to provide a field $H_0$ across the flow line in the sensor and a resonator 111c tuned to the ESR frequency) and detector 112 are used to obtain an ESR signal whose amplitude is proportional to the oil cut. The resonator 111c may be a coil and tuning capacitor or an appropriate cavity, such as a $TE_{102}$ mode, tuned to the ESR frequency. The flow pipe in the sensor is of non-conductive material.

As explained above in connection with FIG. 1, different crude oils have different calibration factors, which are provided to processor 113. The processor 113 is appropriately programmed to calculate the crude oil fraction from the ESR signal amplitude, the dimensions of the pipe, and the calibration factors.

By providing a gradient magnetic field for the ESR sensor, the oil flow velocity may be determined in a manner analogous to the method described above for NMR. The total fluid flow velocity may also be determined by use of a venturi such as that of FIG. 1.

Flowmeter with ESR Sensor and Gamma Ray Sensor

Figure 12:
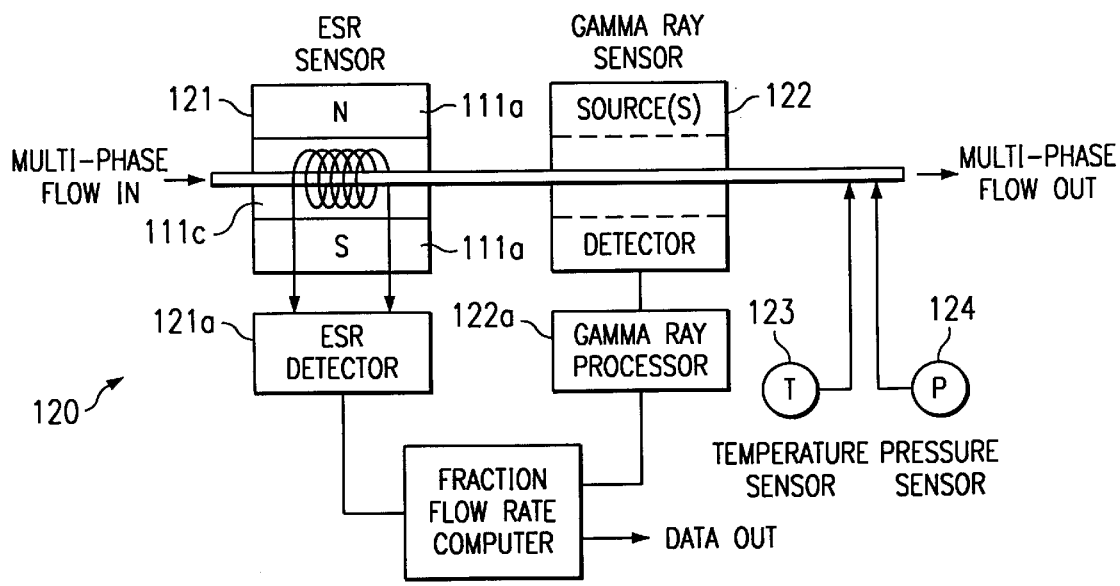
FIG. 12 illustrates a flow meter having an ESR sensor and gamma ray sensor for measuring flow fractions and flow velocities.

FIG. 12 illustrates a flowmeter 120 having an ESR sensor 121 and a gamma ray sensor 122. Each has associated detector electronics 121a and 122a, respectively. ESR sensor 121 provides an ESR signal from which the oil fraction can be calculated as described above in connection with FIG. 11. Gamma ray sensor 122 measures the total fluid density, from which the water fraction and gas fraction are calculated, using temperature and pressure measurements from sensors 123 and 124. The liquid fraction is the difference between the total density and the gas fraction, and the water fraction is the difference between the liquid fraction and the oil fraction. Computer 125 determines the gas, oil, water fractions from the ESR and gamma ray sensor data. Gamma ray processor 126 selects and processes data from detector 122a for use by computer 125.

ESR sensor 121 can also be used to determine the liquid velocity in a manner analogous to the NMR method described above in connection with FIG. 10. In this case, the ESR signals from the fluid would be obtained in a gradient field. If a mixer is used, there is a homogeneous blend of liquids and gas ahead of the ESR sensor, and ESR sensor 121 provides the total velocity of the mixture. Alternatively, a venturi could be used to measure the total velocity of a mixed fluid as described above in connection with FIG. 1.

An advantage of flowmeter 120 is that it does not require a long pre-polarization magnet—the ESR sensor magnet is sufficient. It provides the gas, oil, and water fractions without the need for multi-energy gamma rays, and no separate flow velocity sensor is required.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A flowmeter for a fluid flow having at least one petroleum liquid constituent, comprising:

a pre-polarizer for magnetically polarizing said fluid thereby providing a polarized fluid flow;

a NMR sensor for providing NMR output data from said polarized fluid flow;

an NMR detector for powering said NMR sensor at the NMR frequency and for amplifying and detecting an NMR signal induced in said sensor from said polarized fluid flow;

an ESR sensor for providing ESR output data from said polarized fluid flow;

an ESR detector for powering said ESR sensor at the ESR frequency and for amplifying and detecting an ESR signal induced in said sensor from said polarized liquid flow; and a processor programmed to calculate the total fluid density from said NMR output data, and to calculate the petroleum liquid fraction from said ESR output.

2. The flowmeter of claim 1, wherein said processor is further programmed to calculate a gas fraction of said fluid from said total fluid density and from temperature and pressure measurements.

3. The flowmeter of claim 2, wherein said processor is further programmed to calculate the water fraction from the total liquid density and the oil fraction from said ESR output.

4. The flowmeter of claim 1, wherein said pre-polarizer is comprised of a flowchannel folded in one or more planes and having magnets on opposing sides of said plane.

5. The flowmeter of claim 1, further comprising a mixer for mixing said fluid and a venturi for measuring the total velocity of the mixture.

6. The flowmeter of claim 1, wherein said processor stores calibration data for different types of petroleum liquids and is further programmed to calibrate said ESR output data to determine the fraction of the oil.

7. The flowmeter of claim 1, wherein said processor stores oil identification data is and is further programmed to identify a particular type of said crude oil.

8. A flowmeter for a fluid flow having at least one petroleum liquid constituent, comprising:

a pre-polarizer for polarizing said fluid, thereby providing a polarized fluid flow;

a NMR sensor for providing NMR output data from said polarized fluid flow;

an NMR detector for powering said NMR sensor at the NMR frequency and for amplifying and detecting an NMR signal induced in said sensor from said polarized fluid flow;

an ESR sensor for providing ESR output data from said polarized fluid flow;

an ESR detector for powering said ESR sensor at the ESR frequency and for amplifying and detecting an ESR signal induced in said sensor from said polarized liquid flow; and a processor programmed to calculate the petroleum liquid fraction from said ESR output, and to calculate flow velocity by obtaining a first NMR signal emitted by said polarized fluid that fills said NMR sensor, obtaining a second signal emitted by fluid in said sensor after a delay time that is less than the time required for new polarized fluid to flow into and fill said NMR sensor, and comparing the amplitudes of the second NMR signal and the first NMR signal.

9. The flowmeter of claim 8, further comprising a mixer for mixing said gas and said liquid, such that said flow velocity is of said mixed fluid.

10. The flowmeter of claim 8, further comprising means for stratifying said fluid, such that said flow velocity is stratified liquid.

11. The flowmeter of claim 8, wherein said processor is further programmed to calculate the gas fraction of said fluid from said total fluid density and from temperature and pressure measurements.

12. The flowmeter of claim 11, wherein the gas fraction calculation is based on the difference in amplitudes of the NMR signal component and the NMR signal amplitude from said sensor when filled with liquid.

13. The flowmeter of claim 8, wherein said pre-polarizer is comprised of a flowchannel folded in a plane and having magnets on opposing sides of said plane.

14. The flowmeter of claim 8, wherein said processor stores calibration data for different types of petroleum liquids and is further programmed to calibrate said ESR output data to determine said oil fraction.

15. The flowmeter of claim 8, wherein said processor stores oil identification data is and is further programmed to identify a particular type of said crude oil.

16. The flowmeter of claim 8, wherein said processor determines the water from the total liquid fraction.

17. A flowmeter for a fluid flow having at least one petroleum liquid constituent, comprising:

a pre-polarizer for polarizing said fluid, thereby providing a polarized fluid flow ;

a NMR sensor for providing NMR output data from said polarized fluid flow;

an NMR detector for powering said NMR sensor at the NMR frequency and for amplifying and detecting an NMR signal induced in said sensor from said polarized fluid flow;

an ESR sensor for providing ESR output data from said polarized fluid flow;

an ESR detector for powering said ESR sensor at the ESR frequency and for amplifying and detecting an ESR signal induced in said sensor from said polarized liquid flow; and a processor programmed to calculate the petroleum liquid fraction from said ESR output data and further programmed to calculate the flow rate of said fluid by comparing stored reference data representing a maximum amplitude of an NMR output signal at a known flow rate and a known pulse delay time to said NMR output data acquired after said known pulse delay time.

18. A flowmeter for measuring a fluid flow having at least one petroleum liquid constituent, comprising:

a pre-polarizer for polarizing said fluid, thereby providing a polarized fluid flow within a flow line;

an NMR sensor having a magnet that provides a gradient in the field of said sensor with said gradient causing a variation in the field intensity along said flow line;

an ESR sensor for providing ESR output data from said polarized fluid flow; and a processor programmed to calculate the petroleum liquid fraction from said ESR output data, to provide frequency spectrum data from said NMR data, and to determine the velocity of said petroleum liquid from said frequency spectrum data.

19. A flowmeter for measuring a fluid flow along a flow line, the fluid having at least one petroleum liquid constituent, comprising:

an ESR sensor having a sensor magnet, said sensor providing ESR output data from the fluid flow, and said magnet having a gradient in intensity along said flow line in said sensor, said magnet further providing polarization of the fluid flow;

an ESR detector for powering said ESR sensor at the ESR frequency and for amplifying and detecting an ESR signal induced in said sensor from said polarized fluid flow; and a processor programmed to calculate the petroleum liquid fraction from said ESR output data, to provide frequency spectrum data from said ESR data, and to determine the proportion within the fluid of said petroleum liquid from said frequency spectrum data.

20. The flowmeter of claim 19, further comprising a mixer for mixing the constituents of the fluid upstream of the sensor.

21. The flowmeter of claim 19, wherein said processor stores calibration data for different types of petroleum liquids and is further programmed to calibrate said ESR output data to determine said oil fraction.

22. The flowmeter of claim 19, wherein said processor stores oil identification data and is further programmed to identify a particular type of said crude oil.

23. A flowmeter for a fluid flow having at least one petroleum liquid constituent, comprising:

an ESR sensor for providing ESR output data from said fluid flow;

an ESR detector for powering said ESR sensor at the ESR frequency and for amplifying and detecting an ESR signal induced in said sensor from said polarized liquid flow;

a gamma ray sensor for providing gamma ray output data from said fluid flow; and a processor programmed to calculate the total fluid density from said gamma ray output data, and to calculate the petroleum liquid fraction from said ESR output data.

24. The flowmeter of claim 23, further comprising sensors for measuring the temperature and pressure of said fluid.

25. The flowmeter of claim 23, wherein said processor uses said ESR data to calculate the petroleum liquid fraction, the ESR and gamma ray data to calculate the water fraction, and the ESR and gamma ray data together with fluid pressure and temperature data to determine the gas fraction.

26. The flowmeter of claim 23, wherein said processor stores calibration data for different types of petroleum liquids and is further programmed to calibrate said ESR output data to determine said oil fraction.

27. The flowmeter of claim 23, wherein said processor stores oil identification data is and is further programmed to identify a particular type of said crude oil.

28. The flowmeter of claim 23, further comprising means for providing a gradient polarizing field along a flow line containing said fluid, and wherein said processor is further programmed to provide frequency spectrum data from said ESR data and to determine the velocity of said petroleum liquid from said frequency spectrum data.

29. A method of determining the fractional constituents of a flowing multiphase fluid in situ, said fluid having a liquid petroleum constituent, comprising the steps of:

sensing the total density of said fluid using an NMR sensor;

sensing the density of unpaired electrons using an ESR sensor;

calculating said liquid petroleum fraction from the said density of unpaired electrons; and calculating a gas fraction of said fluid using said total density, and temperature and pressure measurements of said fluid.

30. The method of claim 29, further comprising the step of adjusting said liquid petroleum fraction with a calibration factor for said liquid petroleum constituent.

31. The method of claim 29, further comprising the step of determining a type of said liquid petroleum from characteristics in the output of said ESR sensor.

32. A method of determining the fractional constituents of a flowing multiphase fluid in situ, said fluid having a liquid petroleum constituent, comprising the steps of:

sensing the total density of said fluid using a gamma ray sensor;

sensing the density of unpaired electrons using an ESR sensor;

calculating said liquid petroleum fraction from the said density of unpaired electrons; and calculating a gas fraction of said fluid using said total density, and temperature and pressure measurements of said fluid.

* * * * *